(12) United States Patent
Vanderpohl, III

(10) Patent No.: US 9,569,591 B2
(45) Date of Patent: Feb. 14, 2017

(54) CONFIGURABLE USER INTERFACE SYSTEMS FOR HOSPITAL BED

(75) Inventor: Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 845 days.

(21) Appl. No.: 13/540,140

(22) Filed: Jul. 2, 2012

(65) Prior Publication Data

US 2013/0318716 A1    Dec. 5, 2013

Related U.S. Application Data

(60) Provisional application No. 61/653,726, filed on May 31, 2012.

(51) Int. Cl.
*G06F 19/00* (2011.01)
*A61G 7/018* (2006.01)
*A61G 7/012* (2006.01)
*A61G 7/015* (2006.01)

(52) U.S. Cl.
CPC ........... *G06F 19/3406* (2013.01); *A61G 7/018* (2013.01); *A61G 7/012* (2013.01); *A61G 7/015* (2013.01); *A61G 2203/16* (2013.01); *A61G 2203/20* (2013.01)

(58) Field of Classification Search
CPC ..... G06F 19/3406; A61G 7/018; A61G 7/015; A61G 2203/16; A61G 7/012; A61G 2203/20
See application file for complete search history.

(56) References Cited

U.S. PATENT DOCUMENTS

| | | | |
|---|---|---|---|
| 5,949,982 A * | 9/1999 | Frankeny | G06F 13/4022 710/317 |
| 6,351,678 B1 * | 2/2002 | Borders | A61F 7/007 5/600 |
| 8,046,625 B2 | 10/2011 | Ferguson et al. | |
| 8,308,640 B2 * | 11/2012 | Baldus | G06F 19/323 340/539.12 |
| 8,437,876 B2 * | 5/2013 | Receveur | A61G 7/002 5/600 |
| 8,723,677 B1 * | 5/2014 | Kiani | A61B 5/1115 340/573.1 |
| 2002/0044059 A1 * | 4/2002 | Reeder | A61B 5/0002 340/573.1 |

(Continued)

FOREIGN PATENT DOCUMENTS

| | | |
|---|---|---|
| EP | 2363106 A2 | 9/2011 |
| JP | 2006223649 A | 8/2006 |

OTHER PUBLICATIONS

EP Search Report for EP Application 13169891.2; mailed Nov. 9, 2016; Place of search—The Hague; Date of Completion of Search—Oct. 31, 2016.

*Primary Examiner* — David E Sosnowski
*Assistant Examiner* — Eric Kurilla
(74) *Attorney, Agent, or Firm* — Kenneth C. Baran

(57) ABSTRACT

Configurable user interface systems for a patient support structure are disclosed. As described a control interface comprises the capability to allow limited impact on processes deemed important when other applications and programs are run. The configurable user interface systems described herein allow for customized display of information and display options available to a user in various environments.

27 Claims, 7 Drawing Sheets

(56) References Cited

U.S. PATENT DOCUMENTS

| | | | |
|---|---|---|---|
| 2002/0101619 A1* | 8/2002 | Tsubaki | G06F 17/30265 358/302 |
| 2003/0195644 A1* | 10/2003 | Borders | A47C 31/008 700/90 |
| 2006/0047538 A1* | 3/2006 | Condurso | G06F 19/326 705/3 |
| 2006/0122474 A1* | 6/2006 | Teller | A61B 5/02055 600/300 |
| 2007/0101318 A1* | 5/2007 | Tatsuoka | G06F 9/52 717/135 |
| 2007/0157385 A1* | 7/2007 | Lemire | A61G 7/005 5/600 |
| 2007/0163045 A1* | 7/2007 | Becker | A61B 5/1115 5/616 |
| 2007/0180310 A1* | 8/2007 | Johnson | G06F 15/16 714/12 |
| 2007/0180616 A1* | 8/2007 | Newkirk | A61G 7/018 5/425 |
| 2008/0126132 A1* | 5/2008 | Warner | A61B 5/0002 705/3 |
| 2008/0235872 A1* | 10/2008 | Newkirk | A61G 7/018 5/600 |
| 2009/0044334 A1* | 2/2009 | Parsell | A61B 5/0064 5/424 |
| 2009/0049610 A1* | 2/2009 | Heimbrock | A61G 7/008 5/600 |
| 2009/0112614 A1* | 4/2009 | Guimaraes | G06F 19/322 705/2 |
| 2009/0112630 A1* | 4/2009 | Collins, Jr. | G06F 19/327 705/3 |
| 2009/0119843 A1* | 5/2009 | Rodgers | A61B 5/1115 5/611 |
| 2009/0136094 A1* | 5/2009 | Driver | G06F 19/3406 382/115 |
| 2009/0275808 A1* | 11/2009 | DiMaio | A61B 5/00 600/301 |
| 2010/0212087 A1* | 8/2010 | Leib | G06F 19/327 5/81.1 R |
| 2010/0328034 A1* | 12/2010 | Medina | A61B 5/14551 340/5.83 |
| 2011/0144548 A1* | 6/2011 | Elliott | A61B 5/447 601/49 |
| 2011/0208541 A1* | 8/2011 | Wilson | A61G 7/018 705/3 |
| 2011/0247139 A1* | 10/2011 | Tallent | A61G 7/018 5/613 |
| 2012/0072238 A1* | 3/2012 | Collins, Jr. | G06F 19/327 705/3 |
| 2012/0089419 A1* | 4/2012 | Huster | A61B 5/1115 705/3 |
| 2012/0117730 A1* | 5/2012 | Lemire | A61G 1/0268 5/611 |
| 2012/0141964 A1* | 6/2012 | Lee | G06F 19/3418 434/262 |
| 2012/0216017 A1* | 8/2012 | Inada | G06F 9/5066 712/30 |
| 2013/0019408 A1* | 1/2013 | Jacofsky | A47C 27/083 5/613 |
| 2013/0109929 A1* | 5/2013 | Menzel | G06F 19/3406 600/301 |
| 2013/0239330 A1* | 9/2013 | Newlin | A61G 7/018 5/600 |
| 2013/0283529 A1* | 10/2013 | Hayes | A61G 7/018 5/600 |
| 2015/0186601 A1* | 7/2015 | Waxman | G06F 19/322 705/3 |

* cited by examiner

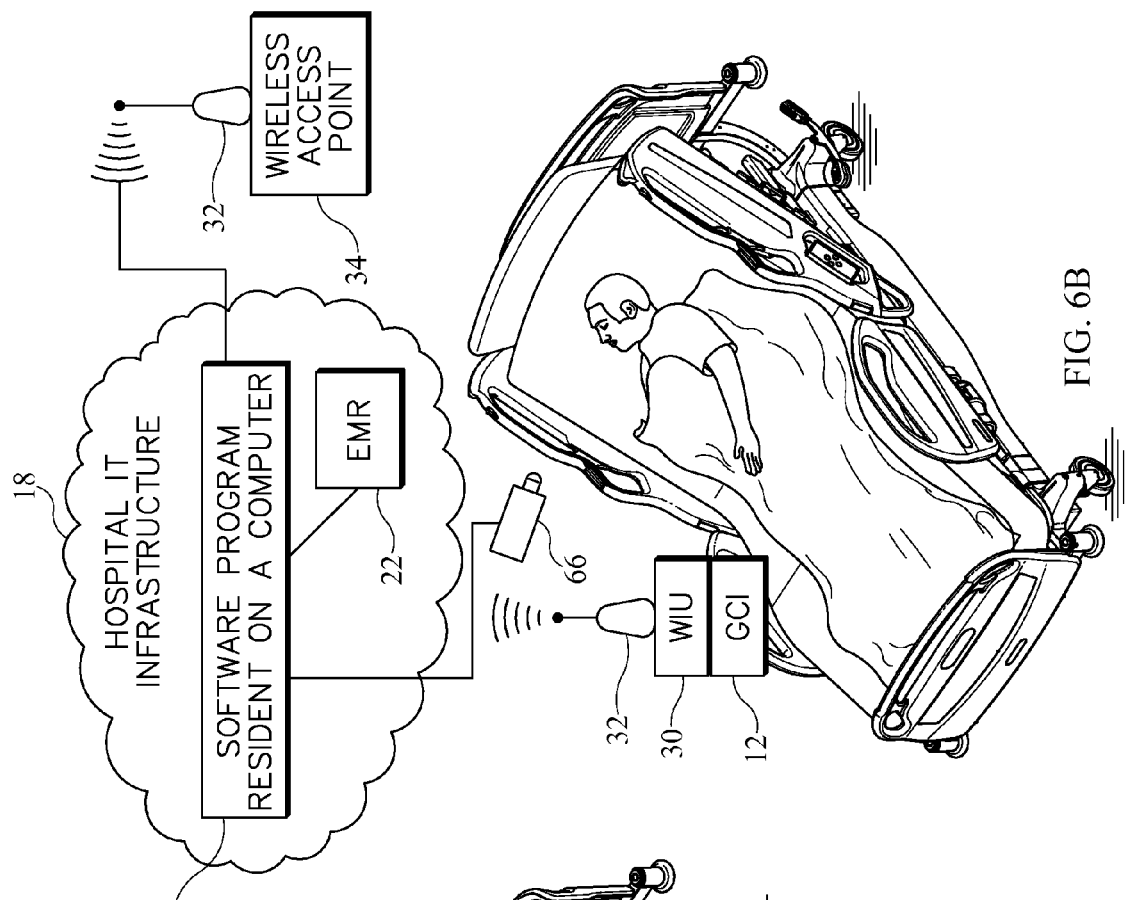
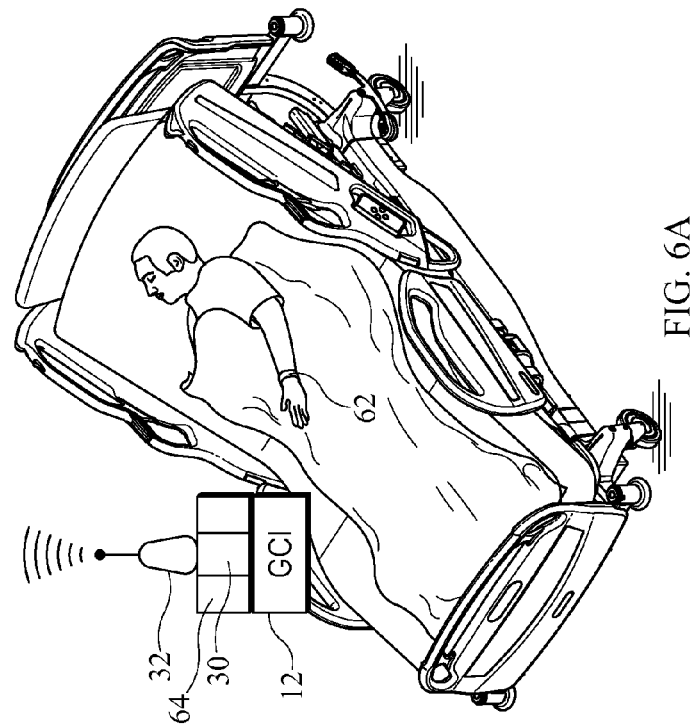
FIG. 6B
FIG. 6A

CONFIGURABLE USER INTERFACE SYSTEMS FOR HOSPITAL BED

CROSS-REFERENCE TO RELATED PATENT APPLICATIONS

This patent application claims the benefit of U.S. Provisional Patent Application 61/653,726, filed on May 31, 2012, the entire disclosure of which is hereby incorporated by reference.

BACKGROUND

The present disclosure relates to hospital beds and particularly the user interface systems for hospital beds. More particularly, the present disclosure relates to configurable user systems for hospital beds. While several systems and methods exist for configuring user systems for hospital beds, a need exists for continued development in this area.

BRIEF SUMMARY

The present disclosure includes one or more of the features recited in the appended claims and/or the following features which, alone or in any combination, may comprise patentable subject matter.

One embodiment of a system for configuring a user interface of a hospital bed may comprise a graphical control interface which may comprise a main processor and an auxiliary processor mounted on a hospital bed. The main processor and the auxiliary processor may be configured to selectively receive information from the software program resident on a computer based on location of said hospital bed. A display device may be configured to be controlled by the graphical control interface based on information received from the software program.

Another embodiment of a system for configuring a user interface of a hospital bed may comprise a main processor and an auxiliary processor. A software program resident on a computer may be configured to selectively send information to the main processor and the auxiliary processor. A display device may be configured to selectively receive information from said main processor and the auxiliary processor; display on said display device may be configured to be controlled by information received from said software program.

Another embodiment of a system for configuring a user interface of a hospital bed may comprise a graphical control interface comprising a main processor and an auxiliary processor. A network interface unit may be configured to communicate with the graphical control interface. A hospital communication network may be configured to communicate with the network interface. The hospital communication network may comprise a software program resident on a computer configured to communicate with the graphical control interface to selectively send information to the main processor and the auxiliary processor. A display device may be configured to selectively receive information from the main processor and the auxiliary processor, display on the display device may be configured to be controlled by information received from the software program.

One embodiment of a configurable user interface for a hospital bed may comprise a main processor and an auxiliary processor which may be configured to communicate with the main processor. A network switch may be configured to selectively transmit information to the main processor and the auxiliary processor based on a control signal received from a software program resident on a computer. A display device may be configured to be controlled by at least one of the main processor and the auxiliary processor, the display on the display device may be configured to be modified based on information received from the software program. A user input receiver may be configured to communicate with at least one of the main processor and the auxiliary processor and may be configured to receive user input.

One embodiment of a system for configuring a user interface of a hospital bed may comprise a graphical control interface which may comprise a main processor and an auxiliary processor mounted on a hospital bed. The main processor and the auxiliary processor may be configured to selectively receive information from the software program resident on a computer based on identity of a patient occupying said hospital bed. A display device may be configured to be controlled by the graphical control interface based on information received from the software program.

One embodiment of a hospital bed may comprise a patient support structure, a graphical interface and control circuitry coupled to the graphical interface, the control circuitry may automatically signal the graphical interface to alter at least one of available control functions displayed on the graphical interface based upon at least one of a location of the hospital bed within a healthcare facility and a type of patient supported on the patient support structure.

One embodiment of a hospital bed may comprise a patient support structure and a graphical interface comprising a main processor which may be configured to process core functions of said patient support structure and an auxiliary processor which may be configured to process additional functions wherein said main processor and said auxiliary processor may be in limited communication with each other, wherein functionality of said main processor may be configured to comply with a regulatory compliance standard.

BRIEF DESCRIPTION OF DRAWINGS

The accompanying drawings incorporated in and forming a part of the specification illustrate several aspects of the claimed subject matter and, together with the description, serve to explain the principles of the claimed subject matter. In the drawings:

FIG. 6A and FIG. 6B are embodiments of a system for configuring a user interface of a hospital bed wherein the user interface is configured based on patient identity, constructed according to one or more of the principles disclosed herein.

DETAILED DESCRIPTION OF ILLUSTRATIVE EMBODIMENTS

Figure 1:
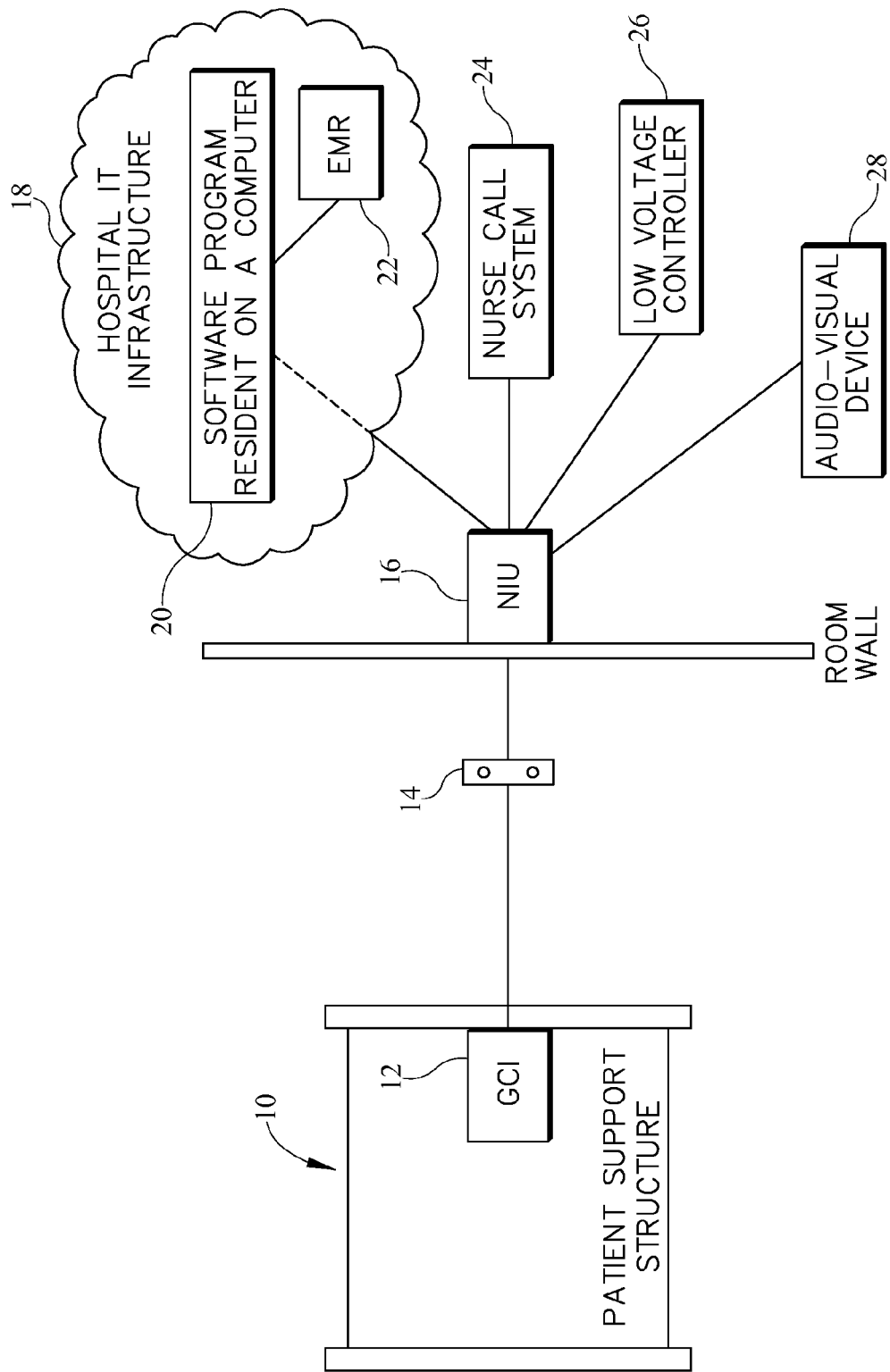
FIG. 1 is a block diagram of a system for configuring a user interface of a hospital bed, constructed according to one or more of the principles disclosed herein.

The embodiments of the claimed subject matter and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be briefly mentioned or omitted so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments described herein are merely illustrative and should not be construed as limiting the scope of the claimed subject matter, which is defined solely by the appended claims and applicable law. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein is used for the purpose of describing particular embodiments only, and is not intended to limit the scope of the claimed subject matter.

Unless defined otherwise, all technical and scientific terms used herein have the same meanings as commonly understood by one of ordinary skill in the art.

According to this disclosure, user interface screens of a hospital bed 10 are configured differently depending on either the location of the hospital bed 10 within a healthcare facility of the type of patient supported on the hospital bed or both. Thus depending upon patient type or location, the user interface screens are altered so that different types of functions are made available on the screen for use by caregivers. Thus patients having different medical conditions or ailments, for example will dictate the features of the hospital bed 10 that are made available for use and/or made unavailable via the graphical user interface of the hospital bed 10.

One embodiment of a system for configuring a user interface for a hospital bed is shown in FIG. 1. As shown in FIG. 1 a graphical control interface (GCI) 12 is mounted on a patient support structure 10. The patient support structure 10 is a hospital bed in this embodiment but may be a wheelchair or a stretcher in other embodiments. The GCI 12 is a screen on which patient information is displayed as well as accepts user inputs such as controlling bed motors to raise and lower an upper frame relative to a base frame, moving mattress support deck sections, controlling mattress therapy functions such as rotation therapy percussion and vibration therapy and alternating pressure therapy. In one embodiment, for patients in traction, some of the screens/functions of the GCI 12 may be completely removed, for example the deck articulation motors should not be moved and patient should not be rotated. The GCI 12 is connected to a network interface unit (NIU) 16 by a wired connection in this embodiment. The GCI 12 is connected to the NIU 16 by an Ethernet cable, while in other embodiments the wired connection may be of any type including but not limited to optical fiber cables. In this embodiment, the Ethernet cable connection between the GCI 12 and the NIU 16 comprises a quick disconnect coupling 14. Quick disconnect coupling 14 is configured to allow the GCI 12 mounted on the bed to separate from the NIU 16 if the bed is wheeled away without damage to the GCI 12, NIU 16 or the cables. Upon the connection between the GCI 12 and the NIU 16 being disrupted, in one embodiment based on decoupling at the quick disconnect coupling 14 the GCI 12 is configured to alter the display into a transport mode. The NIU 16 comprises an Ethernet port in this embodiment, while in another embodiment NIU 16 comprises both the Ethernet port and an Ethernet switch. NIU 16 is located behind the hospital room wall in this embodiment, in other embodiments, NIU 16 may located anywhere including inside the hospital room and/or at a central hospital network station. NIU 16 is connected to the hospital communication network 18 via an Ethernet connection in this embodiment and configured to communicate with a software program 20 resident on a computer. In other embodiments, the software program may be resident on a server or a multitude of computers. The software program 20 is configured to communicate with an electronic medical records (EMR) database 22 as shown in FIG. 1. NIU 16 is also configured to communicate with a nurse call system 24. In this embodiment NIU 16 communicates with the nurse call system 24 via a P379 type connection while in other embodiments NIU 16 may communicate with the nurse call system 24 via any wired or wireless connection. As shown in FIG. 1, NIU 16 is also configured to communicate with a low voltage controller 26 which in this embodiment serves to control the room lighting. NIU 16 is configured to communicate with an audio-visual device 28 which in this embodiment is a television. The GCI 12 allows for control inputs to be sent to the television via the NIU 16 in this embodiment.

Figure 2:
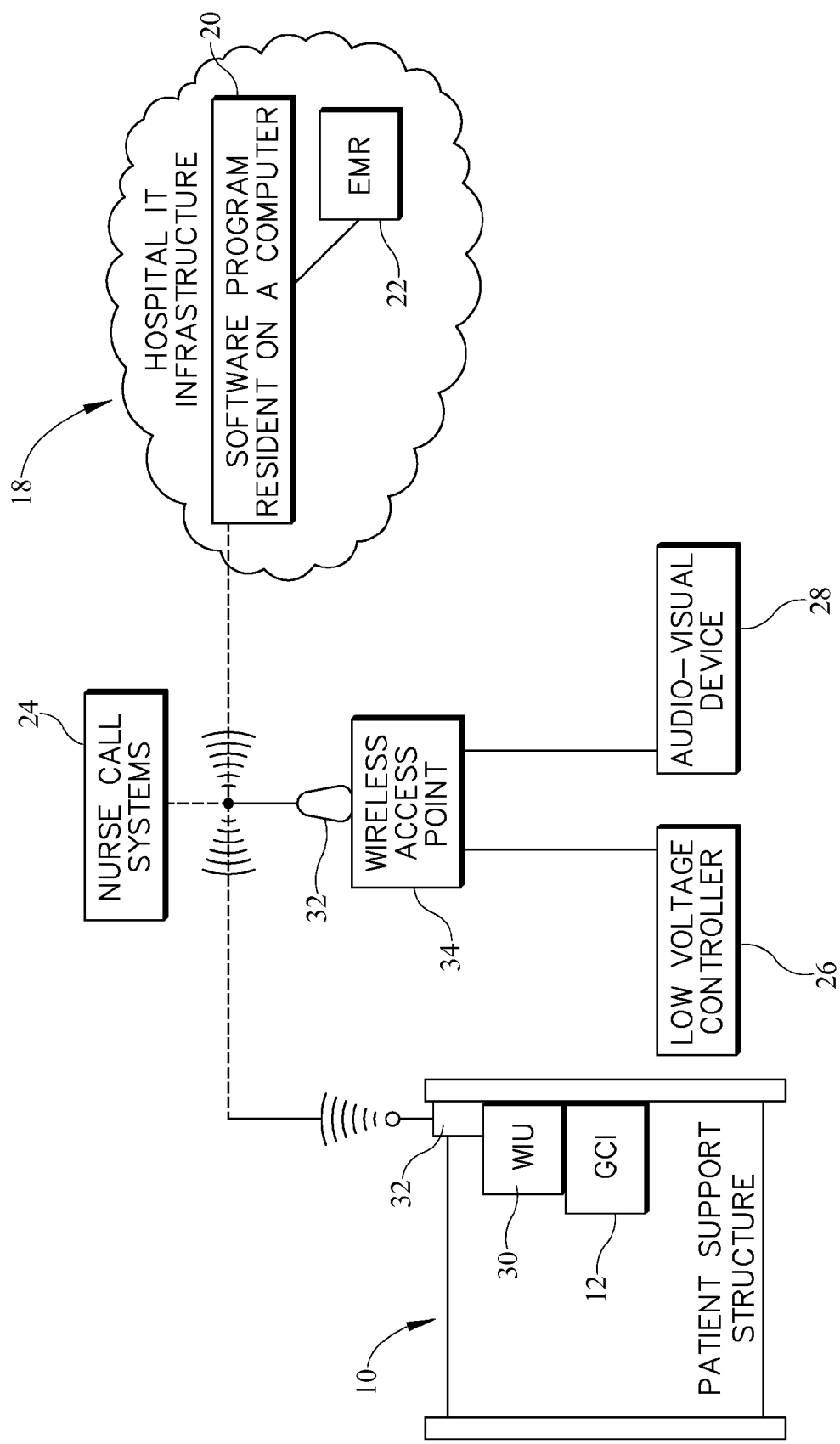
FIG. 2 is another block diagram of a system for configuring a user interface of a hospital bed, constructed according to one or more of the principles disclosed herein.

FIG. 2 shows another embodiment of a system for configuring a user interface for a hospital bed. The GCI 12 is configured to communicate with a wireless interface unit (WIU) 30 which it configured to communicate with a wireless access point 34 by means of antennas 32. Wireless access point 34 is also configured to communicate with a software program 20 resident on a computer which is part of a hospital communication network 18. In this embodiment the wireless access point 34 amplifies and/or filters the signal received from and/or sent to the wireless interface unit 32, in other embodiments the wireless access point 34 serves as a router of the signal received. Software program 20 resident on a computer is configured to communicate with an electronic medical records database 22. In this embodiment the wireless access point 34 is also configured to communicate with a nurse call system 24 and/or a low voltage controller 26 and/or an audio-visual device 28 wirelessly via antenna 32. In other embodiment any of the afore-mentioned connections to and from the wireless access point 34 may be wired.

Figure 3:
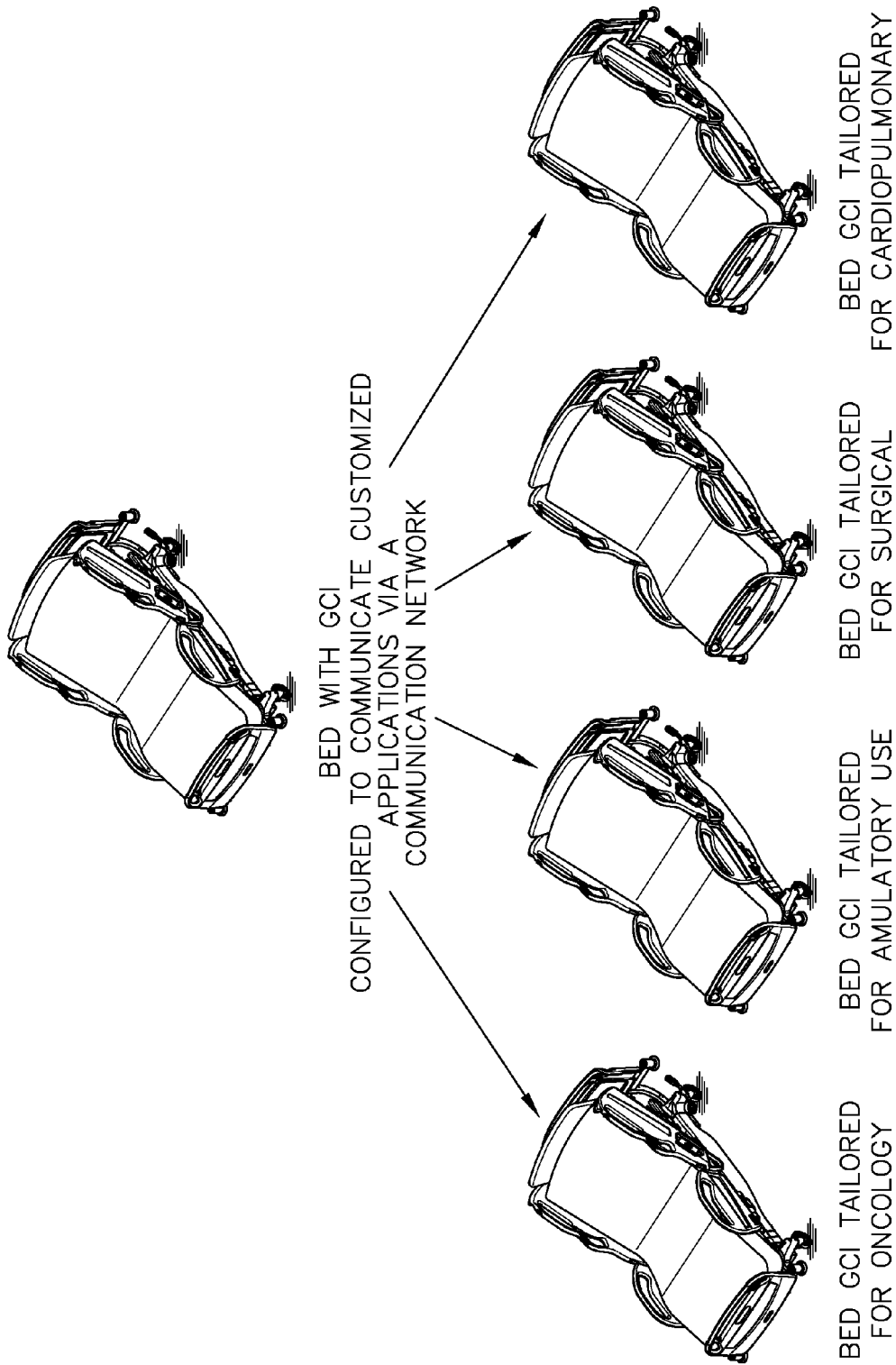
FIG. 3 is a schematic of a hospital bed, the user interface of which is configured to be modified, constructed according to one or more of the principles disclosed herein.

FIG. 3 shows a representational image of a bed with a GCI 12 which is configured to customize the display on a display device 56 based on bed location and/or patient identification and/or caregiver input as shown in FIG. 4 through FIG. 7B.

Figure 4:
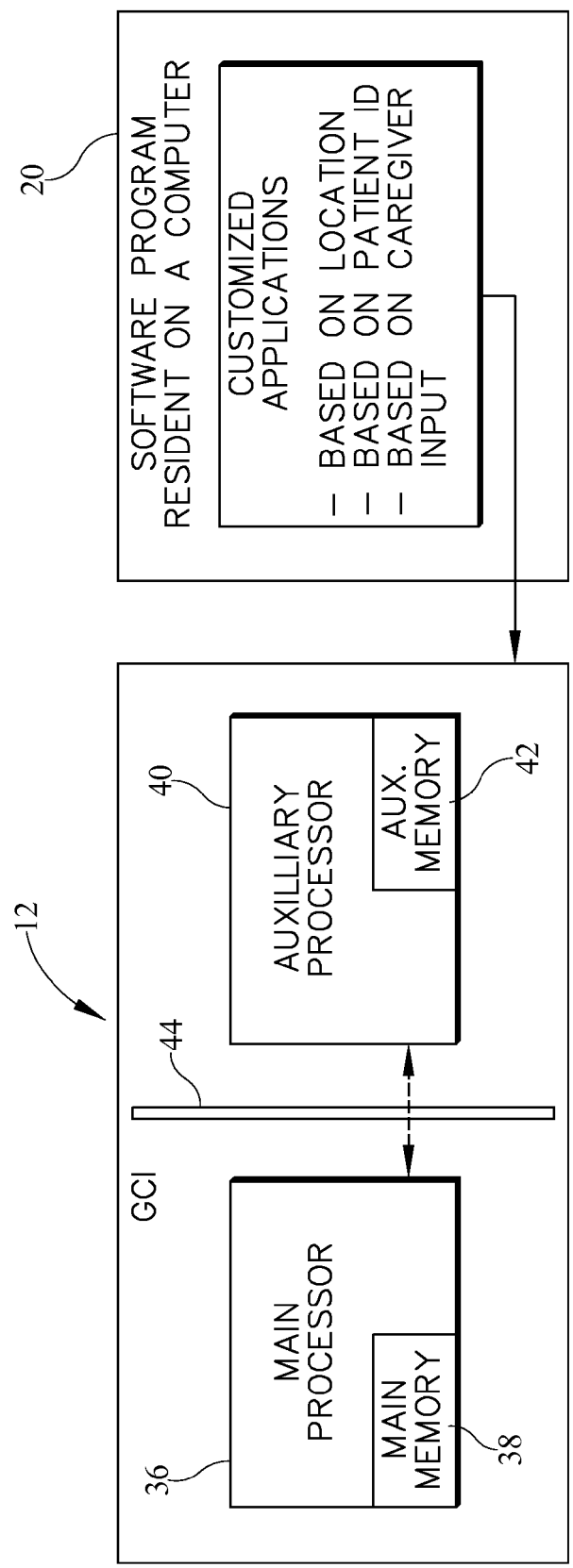
FIG. 4 is another block diagram of some components of the system for configuring a user interface of a hospital bed, constructed according to one or more of the principles disclosed herein.
Figure 5:
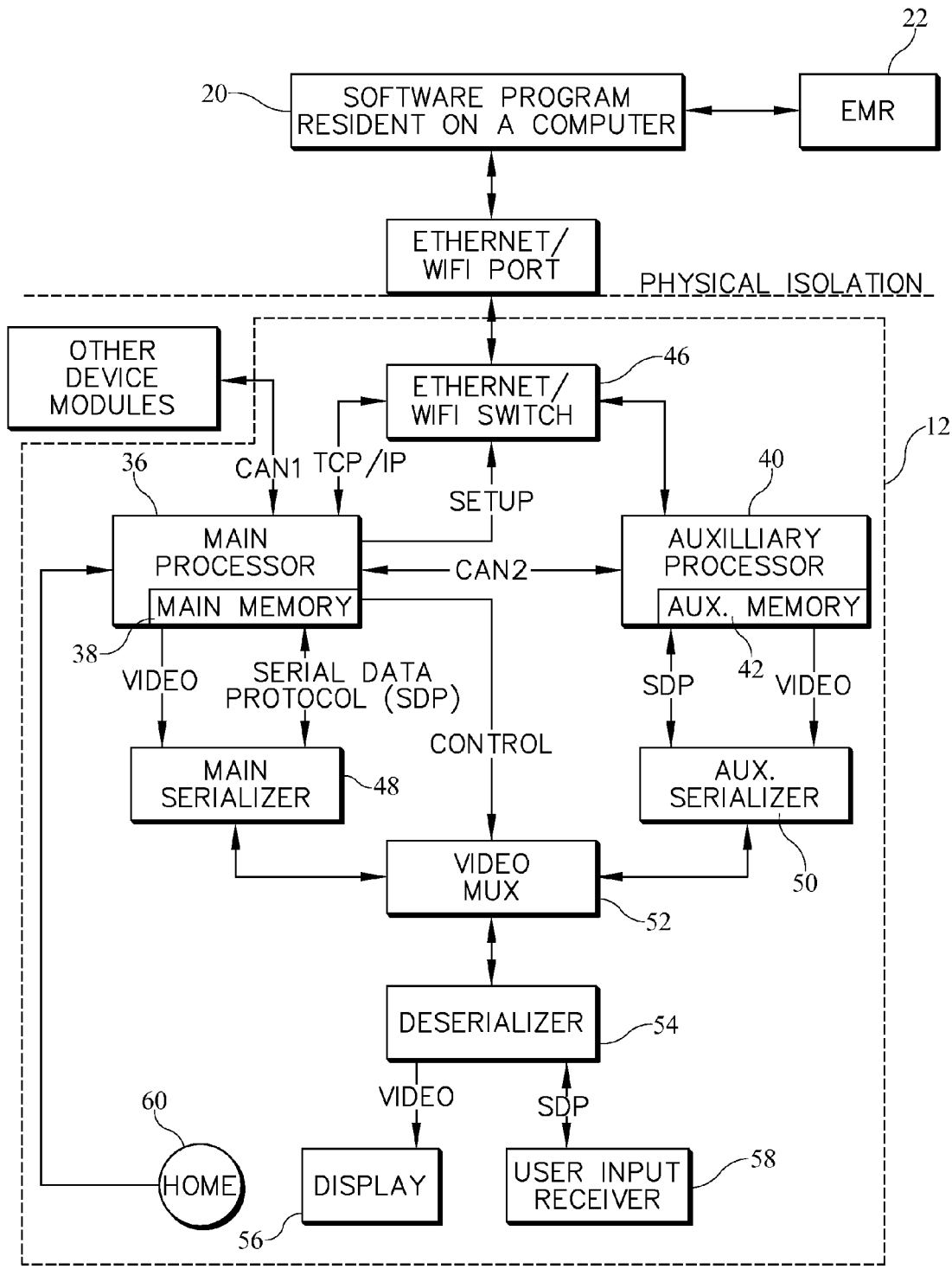
FIG. 5 is a block diagram of a system for configuring a user interface of a hospital bed, constructed according to one or more of the principles disclosed herein.
Figure 7A:
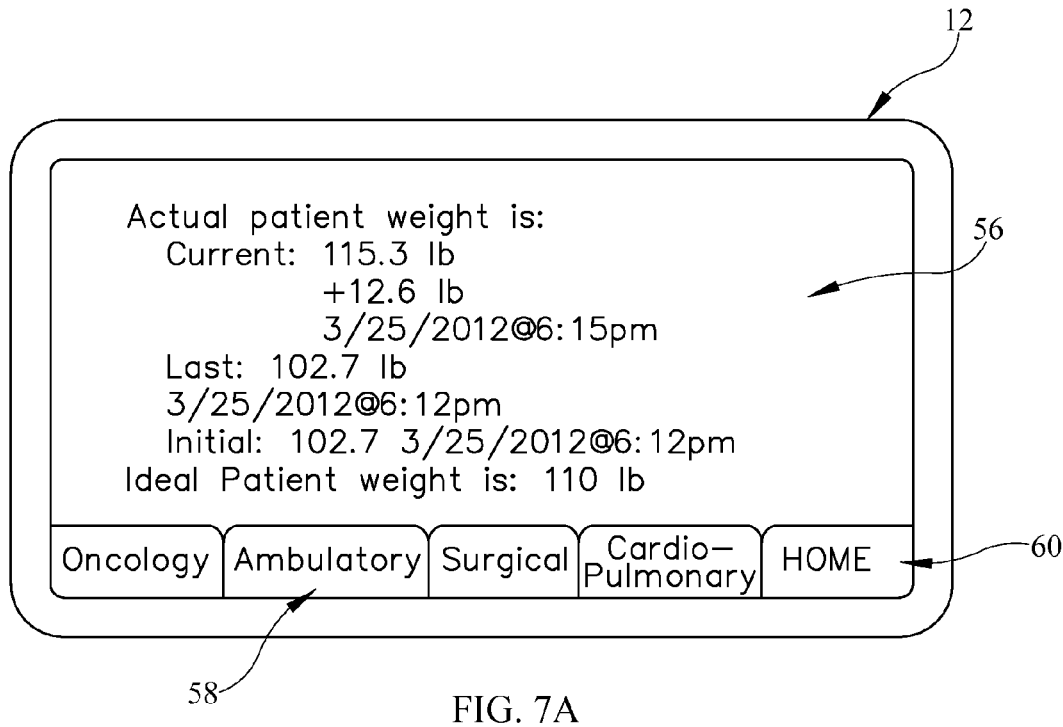
FIG. 7A and FIG. 7B are embodiments of a graphical control interface for use in a system for configuring a user interface of a hospital bed, constructed according to one or more of the principles disclosed herein.
Figure 7B:
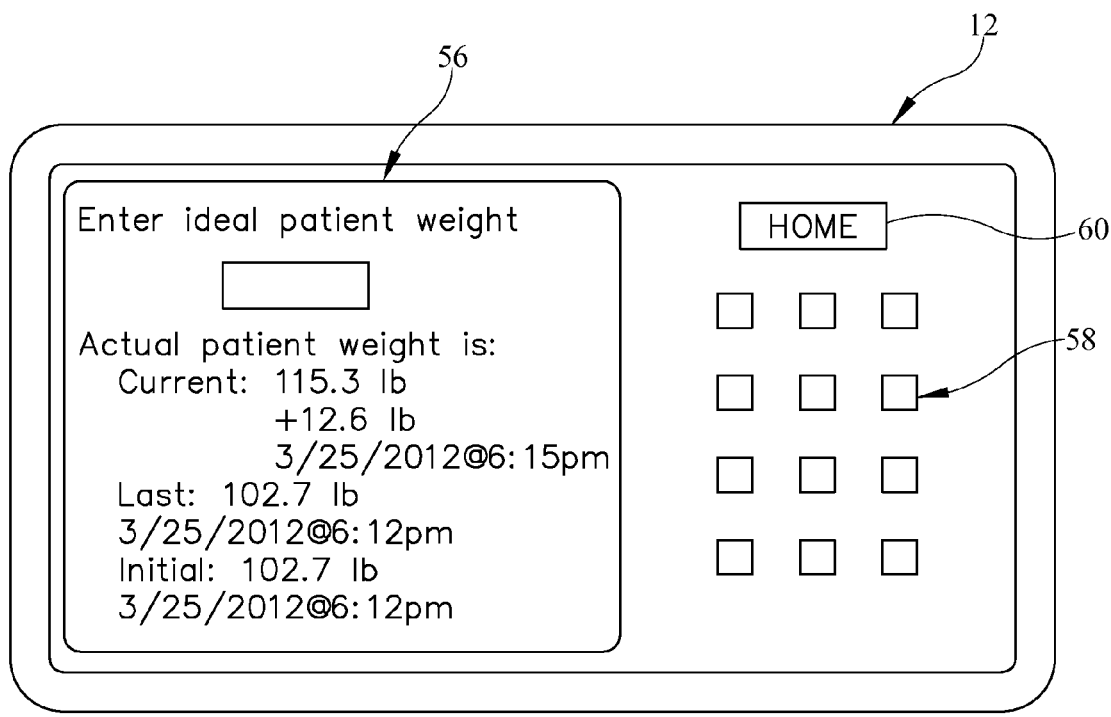

FIG. 4 is another block diagram of some components of the system for configuring a user interface of a hospital bed. As shown in FIG. 4, GCI 12 comprises a main processor 36 with a main memory 38 and an auxiliary processor 40 with auxiliary memory 42. Main memory 38 and auxiliary memory 42 may be volatile and/or non-volatile type. The main processor 36 and auxiliary microprocessor 40 are any programmable or preprogrammed type devices capable of receiving a signal and processing it. In the embodiment shown in FIG. 4, the applications deemed as important to the operation of the patient support structure 10 are processed by main processor 36 and stored in the main memory 38. In this embodiment, the applications include but are not limited to operation of the motors on the patient support structure 10 and/or inflation of the mattress and/or determination of actual patient weight using weighing apparatus integrated in the patient support structure 10. An operating system and/or Controller Area Network (CAN) capabilities and/or Transmission Control Protocol/Internet Protocol (TCP/IP) stack and/or other drivers are also contemplated to be processed by the main processor 36. Several situations may arise wherein customized information or displays may be desirable. In one prophetic example the ideal weight of a patient is desirable since ideal weight correlates to the amount of bone marrow a person has and therefore is useful for calculation of medication dosage. As shown in FIG. 5, FIG. 7A and FIG. 7B the display device 56 may either ask the caregiver to input the ideal weight or the ideal weight is found from the software 20 and/or the electronic medical records 22 and displayed on the display device 56. Auxiliary processor 40 is configured to host applications for customized displays and interfaces such as the case described in the aforementioned prophetic example. In this embodiment the auxiliary processor 40 hosts applications for customized displays as web applications, in other embodiments the applications and/or the web pages are stored in the auxiliary memory 42. Main processor 36 is configured to communicate with the auxiliary processor 40 and logical and/or hardware limitations 44 ensure that communication with auxiliary processor 40 does not overwhelm the main processor 36. Logical or software limits such as the percentage of processing capacity of the main processor 36 that may be occupied in communication with the auxiliary processor 40 ensure that the main processor 36 is not overwhelmed by communication with the auxiliary processor 40. In other embodiments, hardware limits such as physical limitations of the cable and/or other hardware components connecting the main processor 36 and the auxiliary processor 40 ensure that the amount of processing capacity of the main processor 36 that can be used up by the auxiliary processor 40 is limited. This strives to ensure that the main microprocessor 36 has processing capacity accessible to applications deemed as important.

The GCI 12 is in communication with a software program 20 resident on a computer. The software program 20 is configured to communicate alterations to pre-existing applications deemed as important and/or add-on applications and/or third party web applications in various embodiments. The software program 20 is configured to transmit the aforementioned information to the main processor 36 and/or auxiliary processor 40. In this embodiment the software program 20 is configured to communicate the aforementioned information selectively based on location of the patient support structure 10 and/or patient identification and/or caregiver input. In other embodiments, any other criteria may be used to transmit information from the software program 20 and vice versa including but not limited to periodic software updates and maintenance. In the embodiment in which location of the patient support structure 10 causes information to be selectively communicated by the software program 20 to the main processor 36 and/or the auxiliary processor 40, location information may be entered manually or be automatically gathered based on any parameter including but not limited to Media Access Control (MAC) address, IP address, wireless access point information gained from communication between the GCI 12 and the hospital communication network 18. A few examples of tracking and/or location of equipment and personnel are found in U.S. Pat. Nos. 7,450,024, 7,907,053, 7,734,476, and 7,248,933 all of which are incorporated by reference herein. In another embodiment, a dedicated identification device in the room may also be used to determine the location of a patient support structure 10 present in that room relative to its location in the hospital. In one embodiment functionality of the main processor 36 is in compliance with at least one regulatory standard (one prophetic example being the Code of Federal Regulations) while the auxiliary processor 40 functionality does not impact the core functionality of the medical device and the auxiliary processor 40 hosts add-on applications and/or third party web applications not subject to approval and/or compliance requirements.

FIG. 5 shows another block diagram of some components of the system for configuring a user interface of a hospital bed. As shown in FIG. 5, a software program 20 resident on a computer is configured to communicate with an electronic medical records database 22. The software program 20 also communicates with the GCI 12 via an Ethernet and/or wireless networking port. The GCI 12 comprises an Ethernet and/or wireless networking switch 46 which is configured to communicate with the Ethernet and/or wireless networking port, the main processor 36 and the auxiliary processor 40. The Ethernet and/or wireless networking port is electrically isolated from the GCI in this embodiment to allow physical isolation between the bed electronics and the Ethernet and/or wireless networking port. In this embodiment an isolation transformer circuit is used while in other embodiments any other type of physical isolation mechanism may be used including but not limited to a fuse. The aforementioned physical isolation ensures that a sudden spike in voltage and/or current experienced at the Ethernet and/or wireless networking port is not transmitted to the GCI 12. The Ethernet and/or wireless networking switch 46 is controlled by the software program 20 and is configured to selectively communicate information from the software program 20 to main processor 36 and the auxiliary processor 40. In this embodiment the Ethernet and/or wireless networking switch 46 is configured to selectively communicate with the main processor 36 the auxiliary processor 40 by a TCP/IP type of communication protocol, while in other embodiments, the Ethernet and/or wireless networking switch 46 is configured to selectively communicate with the main processor 36 and the auxiliary processor 40 using any type of protocol and/or hardware including but not limited to fiber optical communication. The main processor 36 and the auxiliary processor 40 are in communication via a CAN type connection in this embodiment, while in other embodiments the main processor 36 and the auxiliary processor 40 may be in communication using any other type of connection. Connection between the main processor 36 and the auxiliary processor 40 is limited and is referred to as CAN 2 as opposed to the connections with other device modules which are denoted as CAN1 in FIG. 5. The main processor 36 is also configured to communicate with the Ethernet and/or wireless networking switch 46 to setup communication information. Main processor 36 further comprises a main memory 36 which is configured to store at least one of an operating system, Controller Area Network (CAN) capabilities, Transmission Control Protocol/Internet Protocol (TCP/IP) stack, other drivers, applications and web pages. The auxiliary processor 40 comprises an auxiliary memory 42 which is configured to store web applications, customized applications and web pages in this embodiment. In other embodiments, the main memory 38 and the auxiliary memory 42 are configured to store other information including but not limited to performance data of various components of the patient support structure 10, caregiver input to the GCI 12 and information for other device modules such as a patient identification system.

The main processor 36 and the auxiliary processor 40 are configured to communicate with a video multiplexer 52 via the main serializer 48 and the auxiliary serializer 50 respectively. Main serializer 48 is configured to serialize the video and/or data from the main processor 36. Main serializer 48 is configured to communicate with the video multiplexer 52 to send and receive information. Auxiliary serializer 50 is configured to serialize the video and/or data from the auxiliary processor 40 and is configured to communicate with the video multiplexer 52 to send and receive information. In this embodiment data between the main processor 36 and the main serializer 48 as is data between the auxiliary processor 40 and auxiliary serializer 50 is communicated using Serial Data Protocol (SDP). In other embodiments, any other type of data communication protocol or means may be used. The video multiplexer 52 is in communication with a deserializer 54 which deserializes information received from the multiplexer 52 and is configured to communicate the information to a display device 56. The deserializer 54 also receives data from a user input receiver 58 as shown in FIG. 5. Data received by the desearializer 54 from the user input receiver 58 is transmitted to the video multiplexer 52 and to the main processor 36 and/or auxiliary processor 40 there from. Main processor 36 controls video multiplexer 52 to selectively send information received from the main processor 36 and the auxiliary processor 40 to the deserializer 54. Main processor 36 also controls the flow of information from the video multiplexer 52 to the main processor 36 and/or the auxiliary processor 40. A home button 60 is configured to allow a user to reset the display on the display device 56 to a predetermined state. Home button 60 is a physical hardware component such as a switch, configured to communicate with the main processor 36 in this embodiment. In other embodiments the home button 60 may be an icon on a touch sensitive screen or any other type of switch. The home button 60 allows a user to reset the display on display device 56 and/or the system to a predetermined configuration in case the system 'hangs' or becomes otherwise inoperative.

FIG. 6A & FIG. 6B show embodiments of some components of systems for configuring a user interface of a hospital bed in which the identity of the patient alters the display and/or display options on a display device 56. In another embodiment, identification of the patient supported by the patient support apparatus 10 causes the software program 20 to transmit information to the GCI 12.

As shown in FIG. 6A, an identification tag 62 attached to a person supported by the patient support apparatus 10 allows an identification reader 64 to read the identification tag 62 in this embodiment. In the embodiment shown in FIG. 6A the identification tag 62 is associated with a Radio-frequency ID (RFID) which is recognized by the identification reader 64. The patient is assigned a unique RFID stored in the identification tag 62 upon admission into the hospital or anytime thereafter. In another embodiment the identification tag 62 is associated with the patient support structure 10 and the identity of the patient is determined by the software program 20 by accessing hospital records to ascertain association of a particular patient with a patient support structure 10. In other embodiments, other types of identification tags 62 including but not limited to bar codes may be used along with the corresponding type of identification reader 64. In this embodiment, the identification reader 64 is in communication with the GCI 12 and conveys the unique RFID to the GCI 12. GCI 12 transmits this information to the software program 20 which looks up the relation between the unique RFID and hospital records to establish association between the unique RFID and patient identity. Upon identification of the patient, the software program 20 is configured to transmit information to the GCI 12 which would alter the display and/or display options on a display device 56. In one embodiment the correlation of the patient's identity to a condition and/or ailment results in the user interface being altered.

In the embodiment shown in FIG. 6B, the identity of a patient supported by the person support structure 10 is established by image recognition. An image capture device 66 is configured to capture the image of at least a portion of the patient, in this embodiment the facial region. In this embodiment the image capture device 66 is configured to communicate with a software program 20. The image captured by the image capture device 66 is transmitted to the software program 20 and is compared with a database of patient images. Software program 20 is thereby configured to determine the identity of the patient upon which the software program 20 is configured to transmit information to the GCI 12 which would alter the display and/or display options on a display device 56. In this embodiment the image capture device 66 is configured to transmit information directly to the software program 20, while in another embodiment information from the image capture device 66 is transmitted to the GCI 12 which in turn is communicated with the software program 20. In FIG. 6A and FIG. 6B the communication between the GCI 12 and the software program 20 is shown to be wireless, in another embodiment this communication may be wired.

FIG. 7A and FIG. 7B show two embodiments of a graphical control interface 12. FIG. 7A shows a graphical control interface 12 with a display device 56 which is a touch sensitive screen. In another embodiment, the display device 56 may have the capability to only display images, but not accept user input. In this embodiment the display device 56 comprises a portion of the display represented by selectable buttons which form the user interface receiver 58 portion of the touch sensitive display device 56. In this embodiment, selection of the button labeled Oncology by the user causes the display on the display device to change to a display which has been pre-determined as being Oncology specific. Selection of the Oncology button in this embodiment causes the main processor 36 to control the video multiplexer and allow the pre-determined Oncology specific application stored in the auxiliary memory 42 to be displayed. In another embodiment, selection of the Oncology button by the user is transmitted to the software program 20 which in turn transmits the appropriate information to the main processor 36 and/or the auxiliary processor 40. In the Oncology specific prophetic example of a display screen shown in FIG. 7A, ideal weight of the patient is displayed based on patient identification and by accessing corresponding information from electronic medical records 22. In other embodiments, the ideal weight of the patient may be entered by the caregiver and thereafter stored in the auxiliary memory 42 and/or main memory 38 and/or the software program 20. The home button 60 as shown in FIG. 7A is a display on the user interface receiver portion 58 which in this case is a touch sensitive screen.

In the embodiment of the GCI shown in FIG. 7B, the display device 56 is a liquid crystal display (LCD) screen. As contemplated in the embodiment of the GCI shown in FIG. 7B, location of the patient and/or identity of the patient is determined and in the prophetic example shown in FIG. 7B, an Oncology specific screen is displayed. In this embodiment the caregiver enters the ideal patient weight using the user input receiver 58 which in this case comprises physical buttons. A home button 60 allows the main processor 36 to reset the display 56 to a predetermined state upon activation by the user.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

I claim:

1. A user interface for a hospital bed comprising:
   a display device for displaying control functions related to the bed or an occupant thereof;
   a tag containing bed identification information;
   a reader configured to read the information contained on the tag;
   a software program for establishing a customization to the displayed control functions, the customization being based on at least one of a) location of the bed, and b) occupant identity and wherein the customization is specific to an occupant of the hospital bed and is based on occupant specific information in an information record, the occupant specific information being identified based on an association of the bed with a particular occupant; and
   a control interface comprising a processor which receives a customization command consistent with the customization and controls the display device in response to the customization command so that the displayed control functions depend on the customization command and are customized for the occupant.

2. The user interface of claim 1 comprising a user input receiver capable of receiving user input.

3. The user interface of claim 2 wherein at least a portion of the display device is a touch sensitive screen and serves as the user input receiver.

4. The user interface of claim 1 wherein the customization dictates features of the hospital bed that are made available for use and/or made unavailable for use.

5. The user interface of claim 1 wherein the customization dictates off-bed features that are made available for use and/or made unavailable for use.

6. The user interface of claim 1 wherein the display device is a component of the control interface.

7. The user interface of claim 1 including a tag containing occupant specific information and a reader configured to read the information contained on the tag and wherein the customization is a function of customizing information from the tag.

8. The user interface of claim 1 wherein the customization is also based on occupant identity established by image recognition.

9. The user interface of claim 1 including a main processor and an auxiliary processor each configured to receive the customizing command.

10. The user interface of claim 1 including a main processor and an auxiliary processor and wherein the main processor is configured to process core applications of the bed and wherein the auxiliary processor is configured to process applications for customized displays and interfaces of the display device.

11. The user interface of claim 1 wherein the control interface is mounted on the hospital bed.

12. The user interface of claim 1 including:
   a main processor in compliance with at least one regulatory standard; and
   an auxiliary processor which hosts applications not subject to approval and/or regulatory compliance requirements.

13. A user interface for a hospital bed comprising:
   a display device for displaying control functions related to the bed or an occupant thereof;
   a software program for establishing a customization to the displayed control functions, the customization being based on at least one of a) location of the bed, b) occupant identity and c) user input;
   a control interface comprising a processor which receives a customization command consistent with the customization and controls the display device in response to the customization command so that the displayed control functions depend on the customization command;
   wherein the bed includes a tag containing bed identification information, the user interface includes a reader configured to read the information contained on the tag and wherein the customization is specific to an occupant of the bed and is based on occupant specific information in an information record, the occupant specific information being identified based on an association of the bed with a particular occupant and wherein the displayed control functions are customized for the occupant.

14. The user interface of claim 13 wherein the customization is based on occupant identity established by image recognition.

15. The user interface of claim 13 comprising a user input receiver capable of receiving user input.

16. The user interface of claim 15 wherein at least a portion of the display device is a touch sensitive screen and serves as the user input receiver.

17. The user interface of claim 13 wherein the customization dictates features of the hospital bed that are made available for use and/or made unavailable for use.

18. The user interface of claim 13 wherein the customization dictates off-bed features that are made available for use and/or made unavailable for use.

19. The user interface of claim 13 wherein the display device is a component of the control interface.

20. The user interface of claim 13 wherein the customization is specific to an occupant of the hospital bed and the displayed control functions are customized for the occupant.

21. The user interface of claim 20 including a tag containing occupant specific information and a reader configured to read the information contained on the tag containing occupant specific information and wherein the customization is a function of customizing information from the tag containing occupant specific information.

22. The user interface of claim 13 wherein the customization is also based on occupant identity established by image recognition.

23. The user interface of claim 13 wherein the customization is based on user input and the display is customized based on the user input.

24. The user interface of claim 13 including a main processor and an auxiliary processor each configured to receive the customizing command.

25. The user interface of claim 13 including a main processor and an auxiliary processor and wherein the main processor is configured to process core applications of the bed and wherein the auxiliary processor is configured to process applications for customized displays and interfaces of the display device.

26. The user interface of claim 13 wherein the control interface is mounted on the hospital bed.

27. The user interface of claim 13 including:
 a main processor in compliance with at least one regulatory standard; and
 an auxiliary processor which hosts applications not subject to approval and/or regulatory compliance requirements.

* * * * *